(12) United States Patent
Scott et al.

(10) Patent No.: US 7,927,737 B2
(45) Date of Patent: Apr. 19, 2011

(54) IMPLANTABLE MEDICAL DEVICE AND LITHIUM BATTERY

(75) Inventors: Erik R. Scott, Maple Grove, MN (US); Carl D. Wahlstrand, St. Paul, MN (US); Mark J. Conroy, St. Louis Park, MN (US); John Kast, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 1016 days.

(21) Appl. No.: 11/728,266

(22) Filed: Mar. 23, 2007

(65) Prior Publication Data

US 2007/0248881 A1 Oct. 25, 2007

Related U.S. Application Data

(60) Provisional application No. 60/785,881, filed on Mar. 24, 2006, provisional application No. 60/827,621, filed on Sep. 29, 2006.

(51) Int. Cl.
*H01M 2/26* (2006.01)
*H01M 2/30* (2006.01)
*H01M 4/00* (2006.01)
*A61N 1/00* (2006.01)

(52) U.S. Cl. ........ 429/178; 429/211; 429/161; 429/245; 607/117; 607/119

(58) Field of Classification Search .................. 429/211, 429/178, 194, 7, 53, 152, 164; 428/461; 607/37, 117
See application file for complete search history.

(56) References Cited

U.S. PATENT DOCUMENTS

| | | | |
|---|---|---|---|
| 3,866,616 A | 2/1975 | Purdy et al. | |
| 4,057,679 A | 11/1977 | Dey | |
| 4,989,608 A | 2/1991 | Ratner | |
| 5,154,179 A | 10/1992 | Ratner | |
| 5,167,638 A | 12/1992 | Felix et al. | |
| 5,217,010 A | 6/1993 | Tsitlik et al. | |
| 5,290,266 A | 3/1994 | Rohling et al. | |
| 5,558,641 A | 9/1996 | Glantz et al. | |
| 5,612,152 A * | 3/1997 | Bates ............. | 429/152 |
| 5,817,017 A | 10/1998 | Young et al. | |
| 5,827,186 A | 10/1998 | Chen et al. | |
| 5,864,275 A | 1/1999 | Ohashi et al. | |
| 6,019,737 A | 2/2000 | Murata | |

(Continued)

FOREIGN PATENT DOCUMENTS
EP 0 655 793 B1 5/1995
(Continued)

OTHER PUBLICATIONS

Ida, Nathan, *Engineering Electromagnetics*, $2^{nd}$ Edition, New York, 2004, p. 554.

(Continued)

*Primary Examiner* — Jonathan Crepeau
*Assistant Examiner* — Kenneth Douyette
(74) *Attorney, Agent, or Firm* — Foley & Lardner LLP

(57) ABSTRACT

A lithium battery includes a housing and a first electrode and a second electrode provided within the housing. A first tab is coupled to the first electrode and a second tab coupled to the second electrode. A pin is coupled to the second tab and extends to a location outside the housing. At least one of the first tab, the second tab, and the pin are formed from a material comprising vanadium.

27 Claims, 14 Drawing Sheets

U.S. PATENT DOCUMENTS

| | | | |
|---|---|---|---|
| 6,178,353 | B1 | 1/2001 | Griffith et al. |
| 6,185,446 | B1 | 2/2001 | Carlsen, Jr. |
| 6,458,088 | B1 | 10/2002 | Hurtak et al. |
| 6,527,754 | B1 | 3/2003 | Tallarida et al. |
| 6,765,144 | B1 | 7/2004 | Wang et al. |
| 6,836,683 | B2 | 12/2004 | Nielsen et al. |
| 6,845,259 | B2 | 1/2005 | Pacetti et al. |
| 6,846,985 | B2 | 1/2005 | Wang et al. |
| 7,010,357 | B2 | 3/2006 | Helfer et al. |
| 7,091,412 | B2 | 8/2006 | Wang et al. |
| 7,190,247 | B2 | 3/2007 | Zimmerling |
| 2002/0111617 | A1 | 8/2002 | Cosman et al. |
| 2002/0116033 | A1 | 8/2002 | Greatbatch et al. |
| 2002/0116034 | A1 | 8/2002 | Miller et al. |
| 2002/0128691 | A1 | 9/2002 | Connelly |
| 2002/0162605 | A1 | 11/2002 | Horton, Jr. et al. |
| 2003/0083715 | A1* | 5/2003 | Taylor et al. .................... 607/37 |
| 2003/0100830 | A1 | 5/2003 | Zhong et al. |
| 2003/0111142 | A1 | 6/2003 | Horton, Jr. et al. |
| 2003/0204248 | A1 | 10/2003 | Murphy |
| 2003/0211386 | A1* | 11/2003 | Ruth et al. .................... 429/164 |
| 2004/0142190 | A1* | 7/2004 | Kawai et al. .................... 428/461 |
| 2004/0158309 | A1 | 8/2004 | Wachter et al. |
| 2004/0256131 | A1 | 12/2004 | Wang et al. |
| 2005/0001703 | A1 | 1/2005 | Zimmerling |
| 2005/0043761 | A1 | 2/2005 | Connelly et al. |
| 2005/0090886 | A1 | 4/2005 | MacDonald et al. |
| 2005/0137670 | A1 | 6/2005 | Christopherson et al. |
| 2005/0159661 | A1 | 7/2005 | Connelly et al. |
| 2005/0182482 | A1 | 8/2005 | Wang et al. |
| 2005/0240098 | A1 | 10/2005 | Zhong et al. |
| 2005/0240100 | A1 | 10/2005 | Wang et al. |
| 2006/0105016 | A1 | 5/2006 | Gray et al. |
| 2006/0178708 | A1 | 8/2006 | Rorvick et al. |
| 2006/0217792 | A1 | 9/2006 | Hussein et al. |
| 2007/0043399 | A1 | 2/2007 | Stevenson et al. |
| 2007/0106332 | A1 | 5/2007 | Denker et al. |

FOREIGN PATENT DOCUMENTS

| | | | |
|---|---|---|---|
| WO | WO 9919020 | A1 * | 4/1999 |
| WO | WO 03/039337 | A2 | 5/2003 |
| WO | WO 03/096894 | A1 | 11/2003 |
| WO | WO 2004/093970 | A1 * | 11/2004 |

OTHER PUBLICATIONS

Amendment and Reply for U.S. Appl. No. 11/728,028, filed Sep. 23, 2009, 8 pages.

Amendment and Reply for U.S. Appl. No. 11/728,030, filed Sep. 23, 2009, 15 pages.

Non-Final Office Action and Restriction Requirement for U.S. Appl. No. 11/728,028, mail date Jun. 23, 2009, 15 pages.

Non-Final Office Action for U.S. Appl. No. 11/728,030, mail date Jun. 24, 2009, 16 pages.

Non-Final Office Action for U.S. Appl. No. 11/728,030, mail date Nov. 27, 2009, 13 pages.

Notice of Allowance for U.S. Appl. No. 11/728,028, mail date Nov. 3, 2009, 8 pages.

International Preliminary Report on Patentability for Application No. PCT/US2007/007251, date of mailing Mar. 27, 2008, 6 pages.

International Preliminary Report on Patentability for Application No. PCT/US2007/007384, date of mailing Mar. 10, 2008, 5 pages.

Baba, M. et al., "Multi-layered Li-ion rechargeable batteries for a high-voltage and high-current solid-state power source," *Journal of Power Sources*, Jun. 1, 2003, pp. 914-917, Elsevier Science B.V., Amsterdam, Netherlands, vols. 119-121.

Bates, J.B. et al., "New Amorphous Thin-Film Lithium Electrolyte and Rechargeable Microbattery," Proceedings of the International Power Sources Symposium, Cherry Hill, NJ, Jun. 22-25, 1992, pp. 337-339, New York, IEEE, vol. SYMP. 35.

International Search Report and Written Opinion for Application No. PCT/US2007/007337, mailing date Oct. 16, 2007, 9 pages.

International Search Report and Written Opinion for Application No. PCT/US2007/007384, mailing date Oct. 19, 2007, 8 pages.

International Search Report and Written Opinion for Application No. PCT/US2007/007251, mailing date Sep. 6, 2007, 11 pages.

Amendment and Reply for U.S. Appl. No. 11/728,030, filed Mar. 1, 2010, 13 pages.

Final Office Action for U.S. Appl. No. 11/728,030, dated Apr. 29, 2010, 15 pages.

Amendment and Reply for U.S. Appl. No. 11/728,030, filed Jun. 29, 2010, 14 pages.

Advisory Action for U.S. Appl. No. 11/728,030, dated Jul. 7, 2010, 3 pages.

Request for Continued Examination (RCE) for U.S. Appl. No. 11/728,030, filed Jul. 19, 2010, 4 pages.

Non-Final Office Action for U.S. Appl. No. 11/728,030, dated Aug. 3, 2010, 19 pages.

Amendment and Reply for U.S. Appl. No. 11/728,030, filed Dec. 3, 2010, 13 pages.

Final Office Action for U.S. Appl. No. 11/728,030, dated Jan. 25, 2011, 19 pages.

* cited by examiner

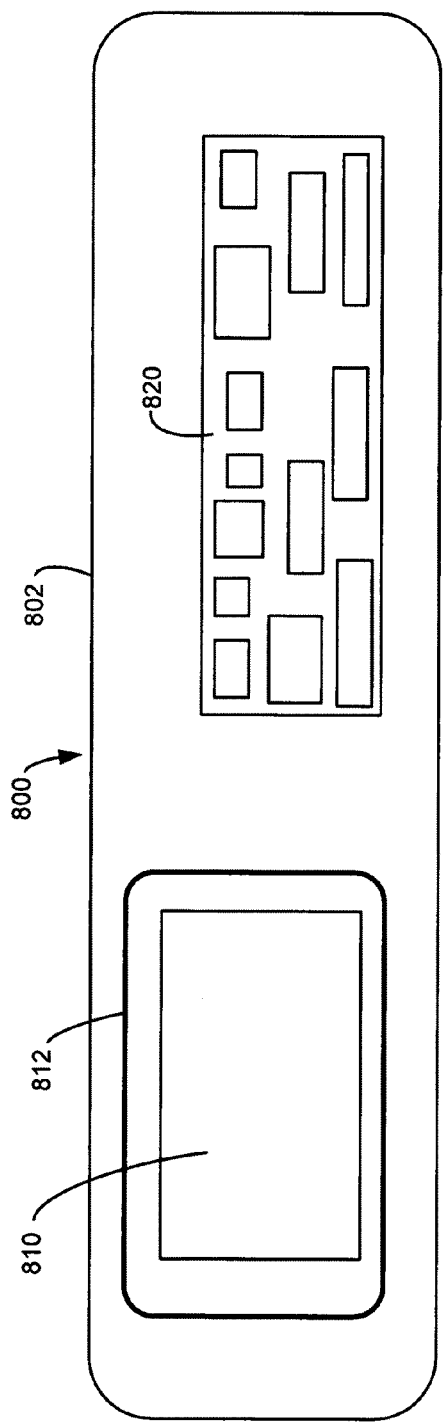
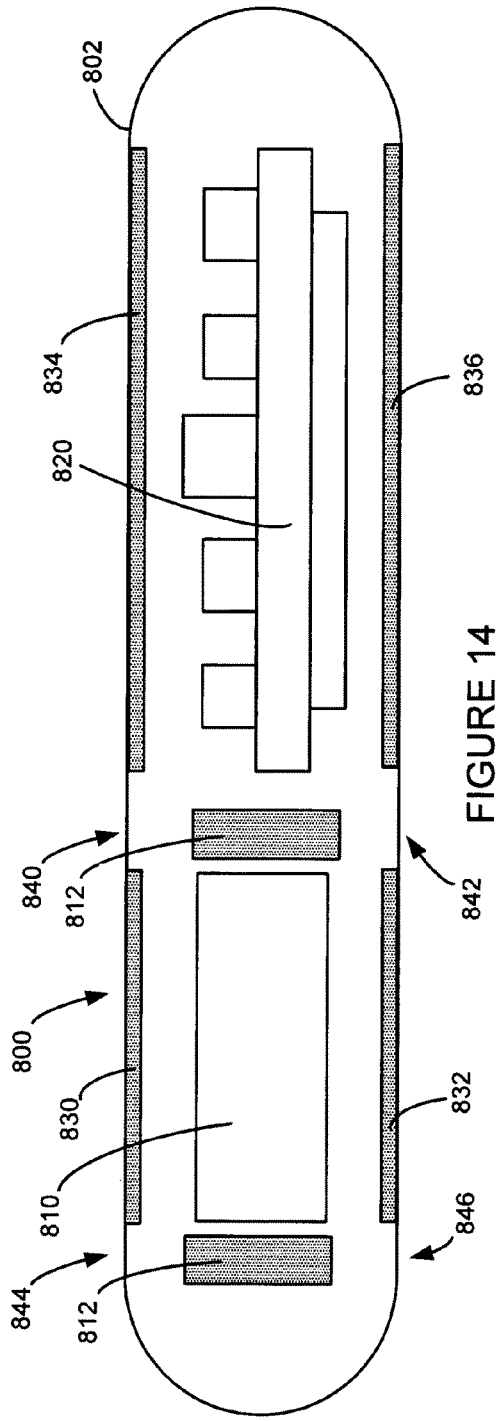
FIGURE 13
FIGURE 14

IMPLANTABLE MEDICAL DEVICE AND LITHIUM BATTERY

CROSS-REFERENCE TO RELATED PATENT APPLICATIONS

The present application claims the benefit under 35 U.S.C. §119(e) of U.S. Provisional Patent Application No. 60/785,881 filed on Mar. 24, 2006 and U.S. Provisional Patent Application No. 60/827,621 filed Sep. 29, 2006, the entire disclosures of which are incorporated herein by reference.

BACKGROUND

The present inventions relate generally to the field of implantable medical devices (IMDs). More particularly, the present inventions relate to IMDs such as implantable neurological stimulation (INS) devices that include features intended to reduce magnetic resonance imaging (MRI) distortion.

Implantable neurological stimulation devices (sometimes referred to as an implantable neuro stimulator or INS) generate electrical stimulation signals that are used to influence the human nervous system or organs. Conventionally, the INS has been surgically implanted into a patient in a subcutaneous pocket in the abdomen, pectoral region, or upper buttocks area. Electrical contacts carried on the distal end of a lead are placed at the desired stimulation site (e.g., at a location in the spine or directly in the brain) and the proximal end of the lead is connected to the INS.

It may be desirable to implant the INS at a location in the patient's head in cases where the distal end of the lead is provided at a site directly in the brain. For example, it may be desirable to implant the INS under the scalp of the patient's head (either on top of the surface of the skull or in a pocket or cutout formed in the skull).

One difficulty with implanting medical devices such as INS devices within the body of a patient is that the materials used in such devices may tend to alter or distort images produced during MRI scans. Such distortion may extend beyond the immediate surrounding area of the device.

Accordingly, there is a need to provide an implantable medical device such as an INS that exhibits reduced image distortion when MRI scans are taken as compared to conventional devices. There is also a need to provide an improved implantable medical device that utilizes different materials for components to minimize MRI image distortion. There is further a need to provide an improved method of performing an MRI scan that provides less image distortion as compared to conventional scanning methods.

SUMMARY

An exemplary embodiment relates to a lithium battery that includes a housing, a first electrode provided within the housing, a first tab coupled to the first electrode, a second electrode provided within the housing, and a second tab coupled to the second electrode. A pin is coupled to the second tab that extends to a location outside the housing. At least one of the first tab, the second tab, and the pin are formed from a material comprising vanadium.

Another exemplary embodiment relates to a lithium battery that includes a housing, a first current collector electrically coupled to a positive electrode, and a second current collector electrically coupled to a negative electrode. A terminal is coupled to one of the first current collector and the second current collector. At least one of the first current collector, the second current collector, and the terminal comprise a material selected from the group consisting of vanadium and vanadium alloys.

Another exemplary embodiment relates to an implantable medical device that includes a housing configured for implantation in a human body. A lithium battery is provided within the housing that includes a member formed of a vanadium material, the member selected from the group consisting of a terminal and a tab for an electrode.

BRIEF DESCRIPTION OF THE DRAWINGS

FIG. 13 is a schematic sectional plan view of an implantable medical device according to an exemplary embodiment.

FIG. 14 is a schematic cross-sectional view of the device shown in FIG. 13 illustrating a shimming material coated or plated on the device housing in locations other than those in which recharge or telemetry coils are provided.

DETAILED DESCRIPTION

According to an exemplary embodiment, an implantable medical device (e.g., an INS) is provided that includes features intended to reduce the amount of MRI image distortion. According to one exemplary embodiment, one or more components of the device may utilize materials or coatings having predefined magnetic permeabilities that are intended to reduce or offset image distortion. According to another exemplary embodiment, one or more components of the device may be configured to reduce the occurrence of eddy currents generated during an MRI scan (e.g., by reducing or varying the thickness of various components).

The human body is composed mostly of water, which has a relative permeability of 0.9999912. Accordingly, water is slightly diamagnetic (see, e.g., Table 1).

TABLE 1

Classification of Materials

| Classification | Diamagnetic | Paramagnetic | Ferromagnetic |
|---|---|---|---|
| Permeability | <1 | >1 | >>1 |

When the human body undergoes an MRI scan, materials having magnetic permeabilities that differ greatly from that of water when the magnetic field is applied will cause distortion in the resulting MRI image. It has been observed that the larger the difference between the magnetic permeability of the material and the magnetic permeability of water at the relatively high magnetic field strengths generated during an MRI scan, the greater the image distortion will be.

Figure 1:
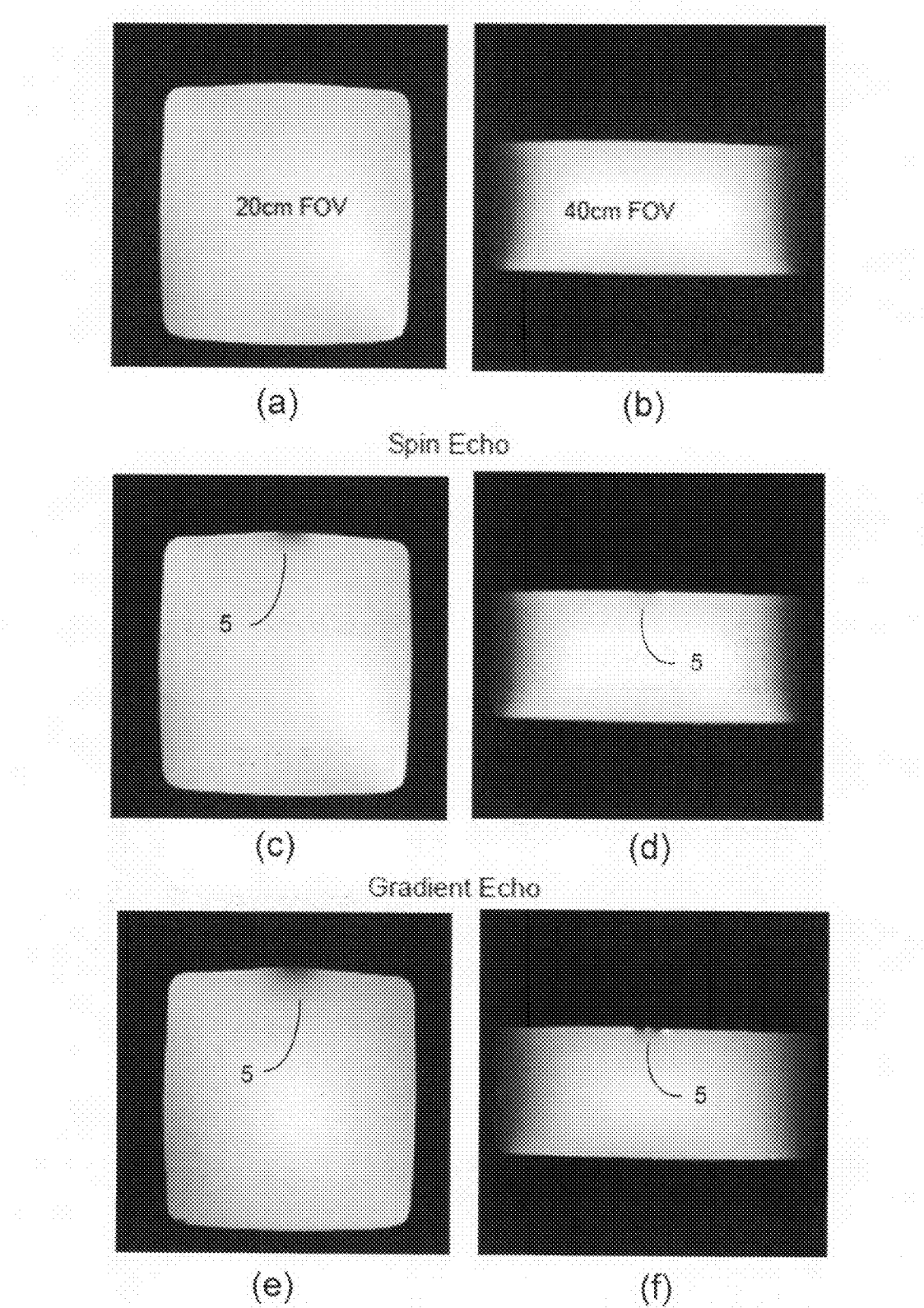
FIGS. 1(a) through 1(f) illustrate MRI image distortion caused by the use of a titanium material.

For example, FIGS. 1(a) and 1(b) illustrate an image taken during an MRI scan (at a magnetic field strength of 1.5 Tesla) of a 20 cm by 40 cm phantom cylinder filled with water to simulate a human head without an implanted INS. FIGS. 1(c) and 1(d) are images taken using a spin echo MRI scan of the phantom cylinder with a titanium can taped to one side of the cylinder. Areas 5 of image distortion are visible in the images as relatively dark portions. Such distortion is increased when using a gradient echo MRI scan, as shown in FIGS. 1(e) and 1(f).

TABLE 2

Relative magnetic permeabilities of selected materials

| Material | Relative Permeability |
|---|---|
| Water | 0.9999912 |
| Copper | 0.9999906 |
| Silver | 0.9999736 |
| Lead | 0.9999831 |
| Air | 1.00000037 |
| Oxygen | 1.000002 |
| Aluminum | 1.000021 |
| Titanium 6-4 (Grade 5) | 1.00005 |

TABLE 2-continued

Relative magnetic permeabilities of selected materials

| Material | Relative Permeability |
|---|---|
| Palladium | 1.0008 |
| Platinum | 1.0003 |
| Manganese | 1.001 |
| Cobalt | 250 |
| Nickel | 600 |
| Iron | 280,000 |

Table 2 lists relative magnetic permeabilities for various materials at relatively low magnetic field strengths (data obtained from various publicly available sources such as http://www.matweb.com). As seen in Table 2, while titanium has a relative permeability of 1.00005, iron (a major component of steel) has a relative permeability of 280,000. As such, it would be expected that including iron in an INS would result in relatively significant image distortion. In general, materials that are ferromagnetic at room temperature—iron, cobalt, and nickel—have relative permeabilities that greatly exceed that of water at relatively high magnetic field strengths, and thus would be expected to distort MRI images far more than materials that have magnetic permeabilities closer to that of water.

Figure 2:
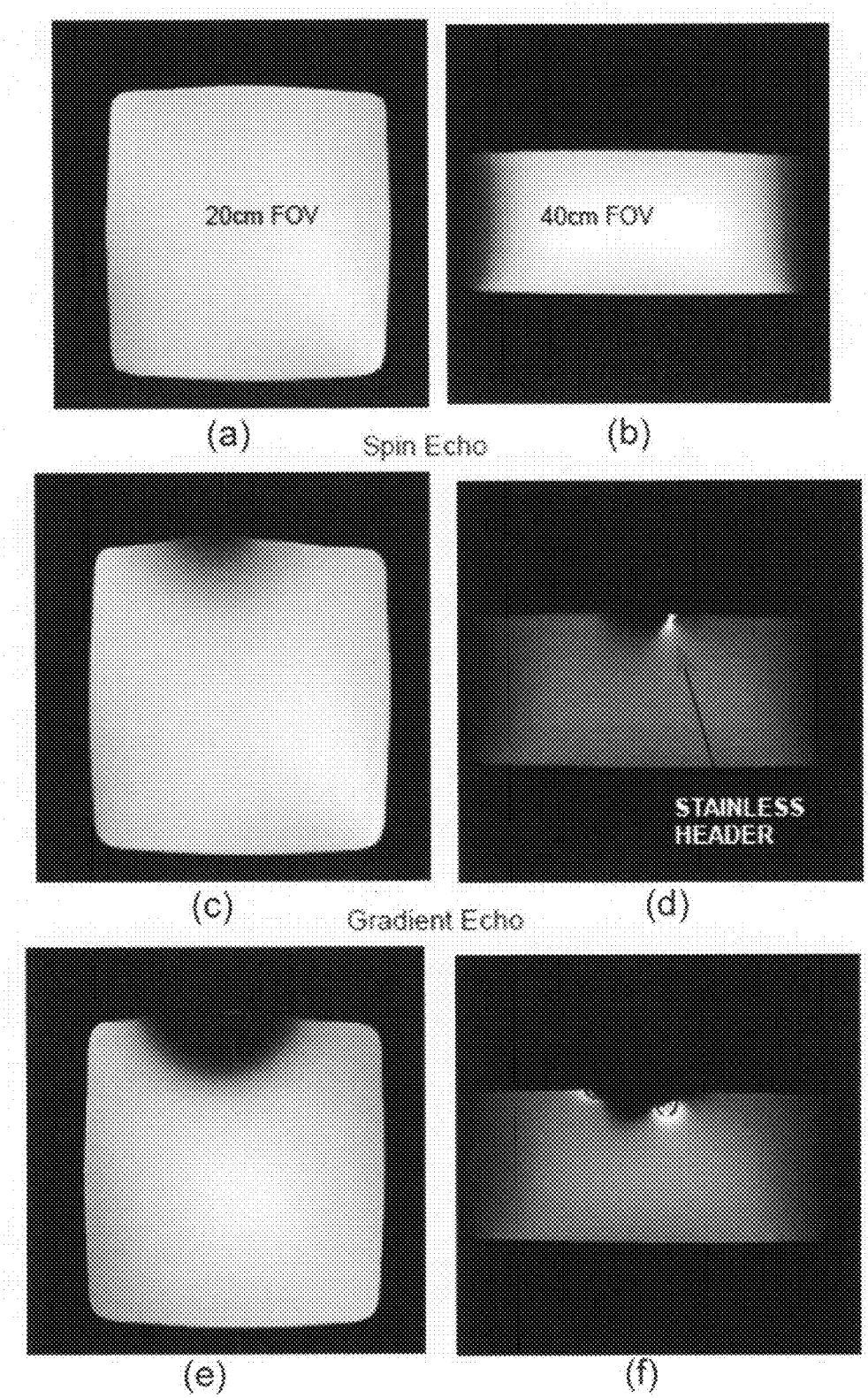
FIGS. 2(a) through 2(f) illustrate MRI image distortion caused by the use of a ferrite material.
Figure 3:
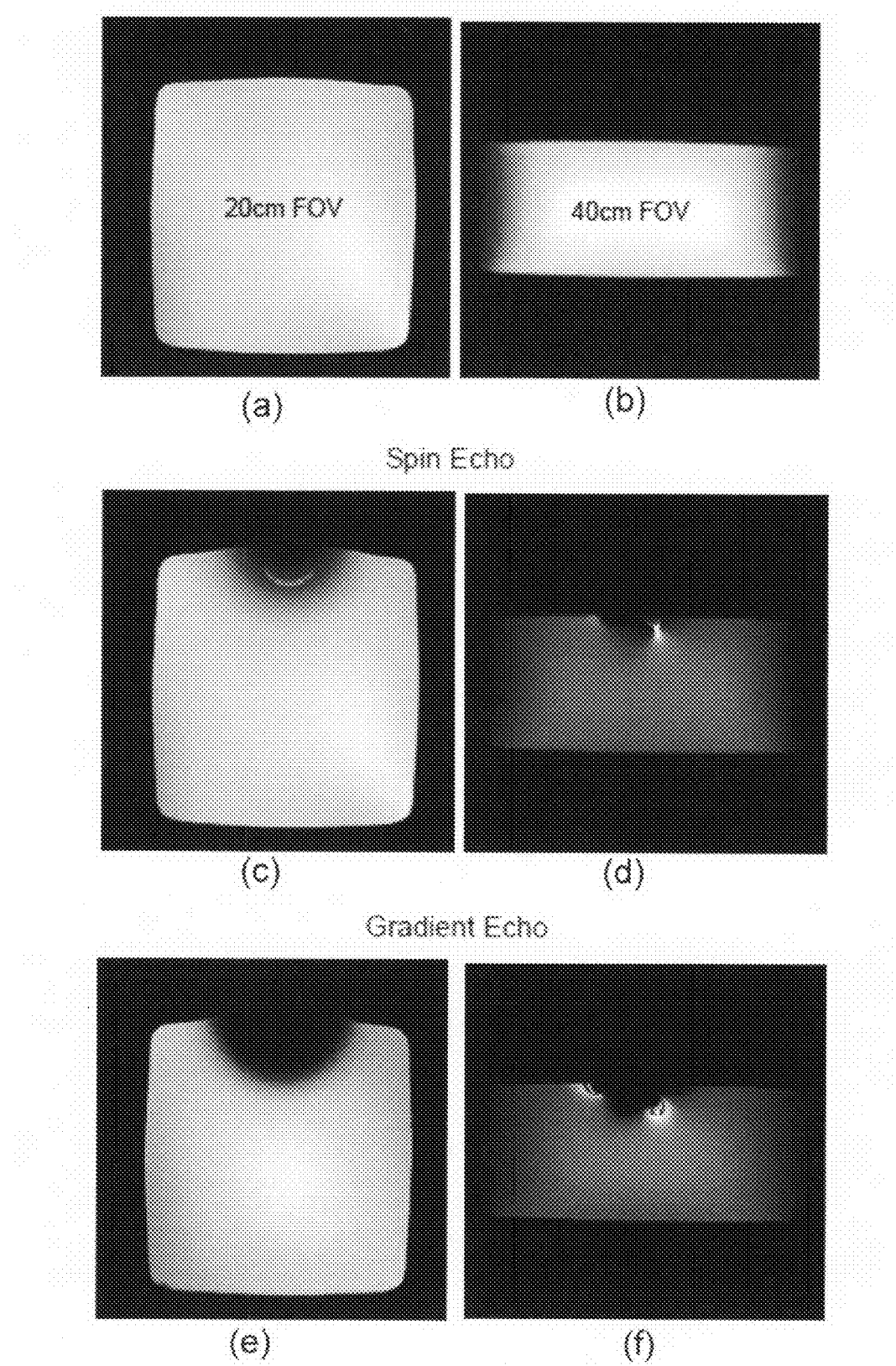
FIGS. 3(a) through 3(f) illustrate MRI image distortion caused by the use of a steel material.

FIGS. 2-3 provide further illustrations of this principle. In contrast to the relatively minor distortion shown in FIGS. 1(c) through 1(f) where a titanium can was coupled to the phantom cylinder, FIGS. 2 and 3 illustrate MRI image distortion resulting from the use of a ferrite material (FIG. 2) and a steel material (FIG. 3) in place of the titanium can (FIGS. 2(a), 2(b), 3(a), and 3(b) are control images similar to those shown in FIGS. 1(a) and 1(b)). As shown in FIGS. 2 and 3, for ferrite and steel materials, the resultant image distortion is far greater than was present using the titanium material.

While the data in Table 2 illustrates relative magnetic permeabilities of various materials, the inventors have observed that certain materials may exhibit different characteristics at the relatively high field strengths used in MRI scans. For example, while Table 2 suggests that copper is slightly diamagnetic at low field strengths, it has been observed that the permeability of copper tends to shift toward being relatively paramagnetic at higher field strengths. In selecting materials as described below (e.g., for use in shimming implantable medical devices), the high-field-strength permeabilities of the materials should be assessed to confirm that such materials will provide the desired effect when subjected to the relatively high magnetic field strengths used in MRI scans.

According to an exemplary embodiment, an implantable medical device may be designed such that it produces less MRI image distortion than would be exhibited by a conventional device. Various different design criteria may be employed in order to accomplish this goal. For example, according to one exemplary embodiment, the amount of ferromagnetic materials (e.g., nickel, cobalt, iron, and ferrites) used in the device may be reduced. While all metals would be expected to produce some degree of MRI image distortion, reducing the amount of ferromagnetic materials would have a greater effect on image distortion than reducing the amount of slightly diamagnetic and paramagnetic materials.

It may also be desirable to minimize the eddy currents that may be induced during imaging. Eddy currents cause distortion, although such distortion is not expected to be as significant as that caused by ferromagnetic materials. Reducing the eddy currents associated with a particular device may be accomplished principally by reducing or varying the thickness of various components as compared to conventional components.

It may also be desirable to remove or shim non-ferromagnetic materials that have permeabilities that differ from that of water. For example, relatively large components that are made of paramagnetic materials may be shimmed with a diamagnetic material to balance out the paramagnetic material and to reduce image distortion. According to an exemplary embodiment, materials that have permeabilities that differ from water at high field strengths (e.g., 1.5 or 3 Tesla) such as those found in MRI imaging applications may be shimmed, removed from the device, or made of materials less likely to cause significant image distortion.

Figure 4:
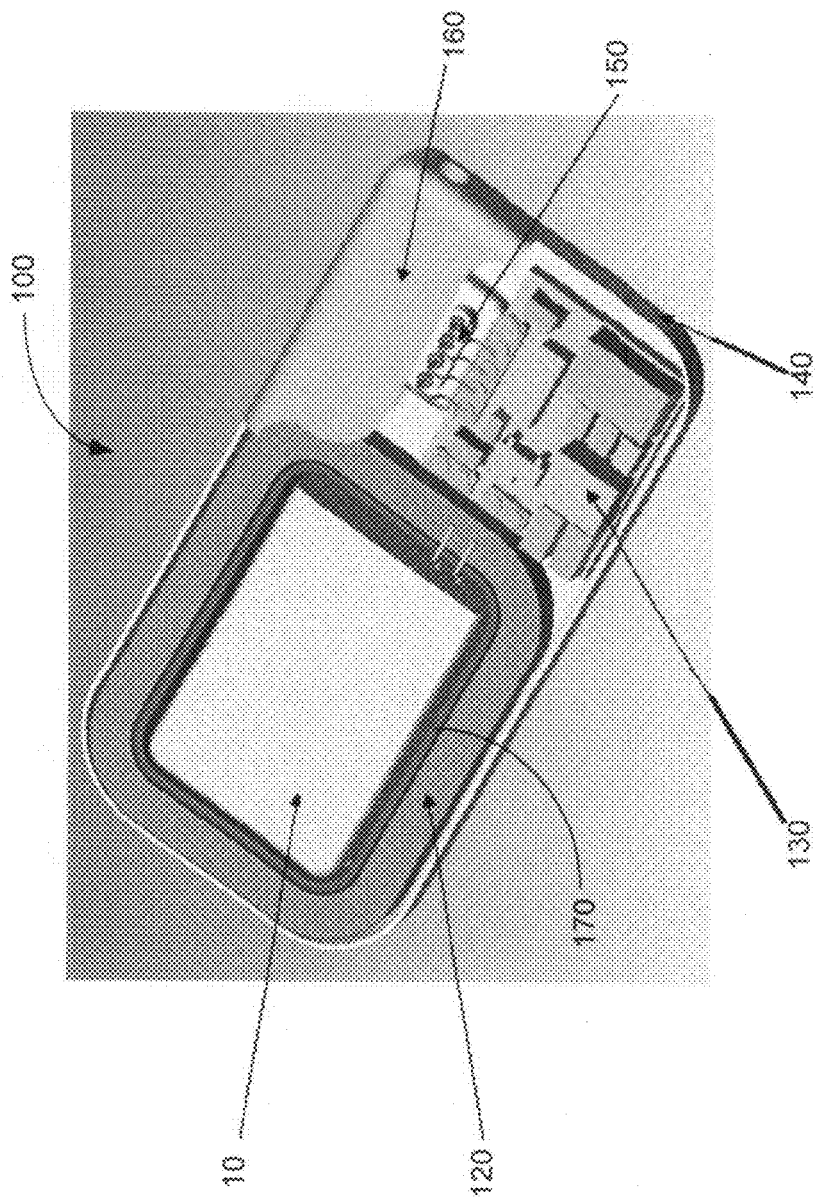
FIG. 4 is a cutaway perspective view of an implantable medical device in the form of an INS according to an exemplary embodiment.

FIG. 4 illustrates an implantable medical device 100 in the form of an implantable neurological stimulation (INS) device according to an exemplary embodiment. As shown in FIG. 4, the device 100 includes a battery 10, coils 120 (e.g., for recharging the battery or for telemetry), a wiring board or hybrid 130 (e.g., a circuit board having various electronic components soldered or otherwise provided thereon), a device enclosure 140 (e.g., a housing or casing), interconnects 150, and a connector or header 160 (the connector includes an aperture as shown at the right side of FIG. 4 that is configured to have a lead inserted therein).

Figure 5:
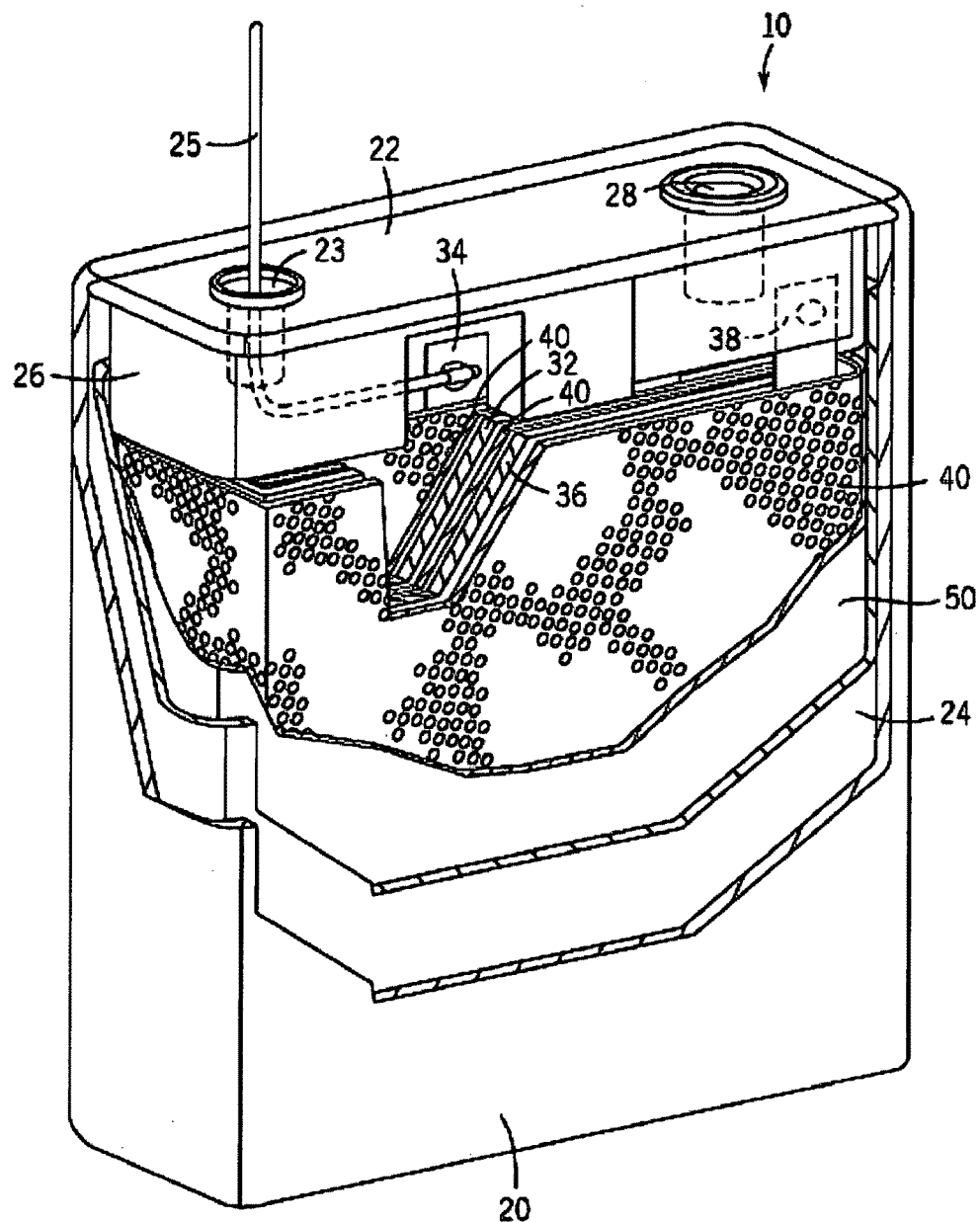
FIG. 5 is a partial cutaway perspective view of a battery configured for use in an INS shown such as that shown in FIG. 4 according to an exemplary embodiment.
Figure 6:
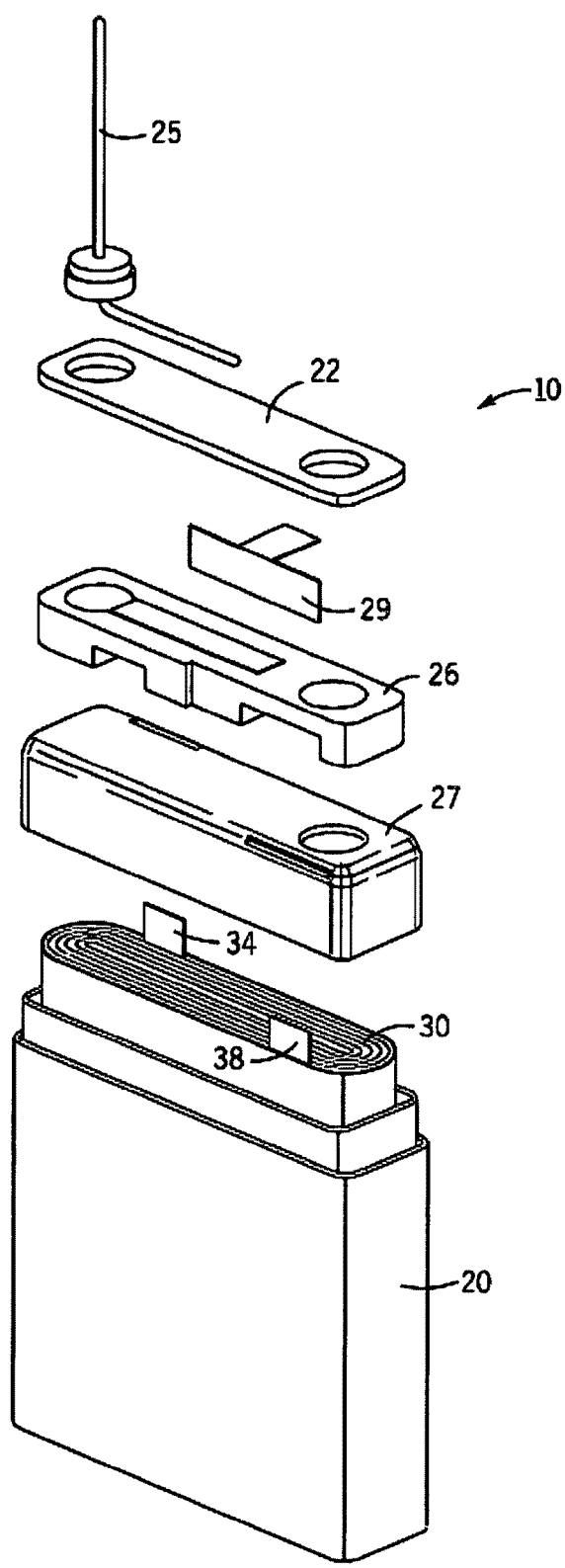
FIG. 6 is an exploded perspective view of the battery shown in FIG. 5 according to an exemplary embodiment.

FIGS. 5-6 provide further illustrations of the components of the battery 10 that may be used in conjunction with device 100. It should be noted that the battery 10 may be a non-rechargeable (i.e., primary) or a rechargeable (i.e., secondary) lithium-based battery according to various exemplary embodiments.

With reference to FIG. 5, the battery 10 includes a battery case or housing 20 provided in the form of a relatively thin-walled hollow structure that is configured for having a plurality of components provided therein. A liner 24 is provided adjacent or proximate the housing 20 to separate internal components of the battery 10 from the housing 20. A cover or cap 22 is provided at a top surface of the battery 10 and may be coupled (e.g., welded, adhered, etc.) to the housing 20. A headspace insulator 26 is provided within the housing 20 to provide a space in which connections may be made to electrodes provided within the housing 20 (additionally, a coil liner 27 as shown in FIG. 6 may be provided which may act to separate a cell element from the headspace region of the battery 10). A member or element 29 in the form of a bracket may be provided to couple a current collector of a negative electrode to the case and/or to the housing.

The battery 10 includes a cell element 30 provided within the housing 20 that comprises at least one positive electrode and at least one negative electrode. Each of the electrodes has a member or element in the form of a tab or current collector coupled thereto. As illustrated in FIGS. 5-6, electrode 32 is a positive electrode having tab 34 coupled thereto, and electrode 36 is a negative electrode having a tab 38 coupled thereto. In such a configuration, the battery 10 has a case negative design. According to other exemplary embodiments in which the battery includes a case positive or neutral design, the electrodes may be reversed (e.g., electrode 32 would be the negative electrode and electrode 36 would be the positive electrode).

The current collector 34 of the positive electrode is electrically coupled to a pin or terminal 25 (e.g., a feedthrough pin) that is provided such that it protrudes through an opening or aperture 23 provided in the cover 22. In such an embodiment, the pin would act as the positive terminal for the battery and may be connected at a distal end to a feature included in a hybrid (either directly or indirectly). In a case neutral or case positive battery design, the pin 25 may be coupled to a tab provided on a negative electrode.

A separator 40 is provided intermediate or between the electrodes, and an electrolyte 50 is also provided in the housing 20 (e.g., through an opening or aperture 28 in the form of a fill port provided in the cover 22 of the battery 10).

In conventional lithium batteries used in implantable medical device applications, the housing of the battery is made from a metal such as stainless steel. To reduce the image distortion caused by the battery 10, the housing 20 may be made of a material that is less likely to result in substantial MRI image distortion such as one or more of the following materials: (1) aluminum or an aluminum alloy (including the 3000 series); (2) aluminum foil/polymer composites with heat-sealable edges (i.e., a "foil pack"); (3) titanium and titanium alloys (alloys include Grade 5, Grade 9, Grade 1, and SP700 (Ti-4.5Al-3V-2Mo-2Fe)); and (4) copper and copper alloys.

Figure 20:
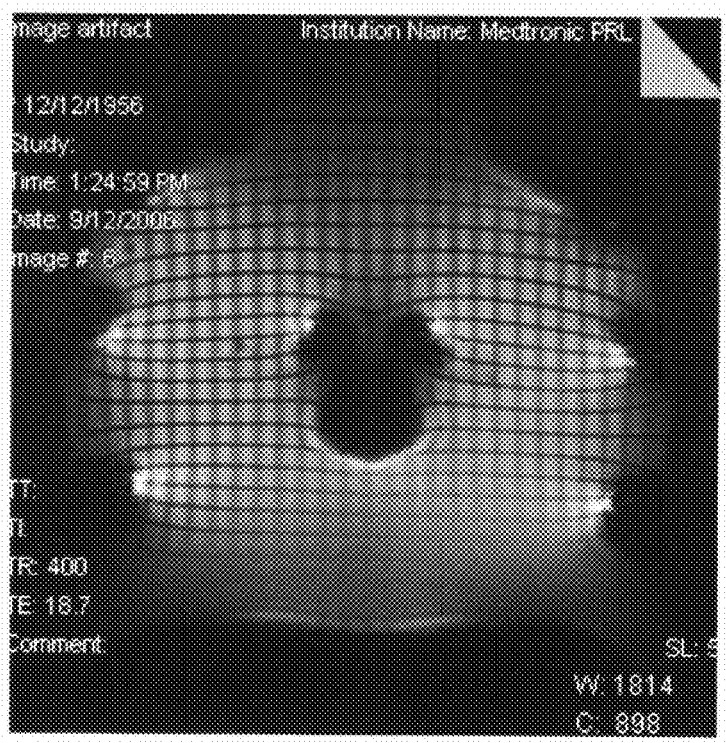
FIG. 20 is an MRI image of a battery housing or casing made of stainless steel.
Figure 21:
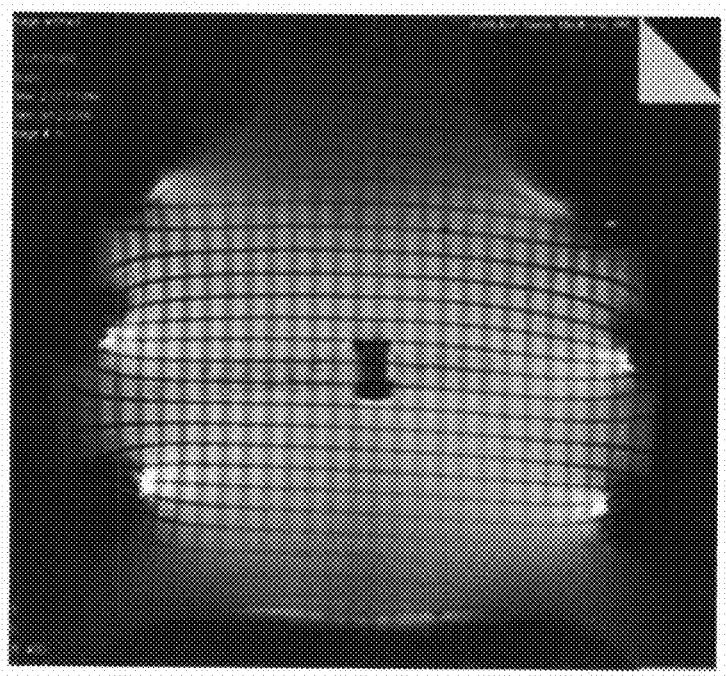
FIG. 21 is an MRI image of a battery housing or casing made of an aluminum housing.

It should be noted that for reasons of electrochemical stability, some case materials should only be used at one or the other of the battery polarities, or at a neutral potential. For example, for many lithium-based battery configurations, aluminum may be an inappropriate housing material if the housing 20 is at the negative polarity of the cell, and stainless steel or titanium would be inappropriate at the positive cell polarity. This housing material choice depends on battery chemistry and knowledge of material stability. FIGS. 20 and 21 illustrate MRI images taken of a stainless steel battery case (FIG. 20) and an aluminum battery case (FIG. 21). As shown, the amount of distortion caused by the aluminum battery case is significantly less than that caused by the stainless steel battery case.

Other components of the battery 10 may also be formed of materials that are less likely to cause significant MRI image distortion. For example, according to an exemplary embodiment, components such as the pin 25 (which is conventionally made of a titanium alloy or niobium), the tabs 34, 38, and the bracket 29 may be made of aluminum, copper, vanadium, or alloys and combinations thereof, and the header and fill port 28 may be made one or more of the materials described above with respect to the housing 20.

According to an exemplary embodiment in which a battery has a case negative design, the tab coupled to the negative electrode (e.g., tab 38 as shown in FIG. 6) may be formed of vanadium or a vanadium alloy. According to another exemplary embodiment in which the a battery has a case neutral or case positive design, the pin 25 and/or the tab coupled to the negative electrode (which would be tab 34 as shown in FIG. 6, since the electrodes would be reversed in such a configuration) may be formed from vanadium or a vanadium alloy. According to another exemplary embodiment, the tab coupled to the positive electrode may be formed from vanadium or a vanadium alloy where the potential of the positive electrode does not exceed approximately 3.6 volts (i.e., does not exceed the corrosion potential of vanadium). Other features of the battery 10 may also be formed of vanadium or a vanadium alloy according to other exemplary embodiments, such as the housing 20 or the cover 22.

One advantageous feature of using vanadium is that in addition to being beneficial for reducing MRI image distortion, vanadium may also be welded to both copper and titanium (e.g., which would allow a case-negative design with a titanium case such that vanadium could be welded from a copper electrode to the titanium case). In other applications, a case-positive design may be used in which an aluminum interconnect from an aluminum positive electrode could be welded to an aluminum case.

The conductors that connect the pin 25 to the hybrid 130 may be made of aluminum, copper, titanium, vanadium, or alloys thereof. Alternatively, the pin 25 may be connected directly to the hybrid 130 without the need for separate connectors. In another example, non-ferrous conductors such as titanium or titanium alloys may be used to connect the pin 25 to the bal-seals.

According to an exemplary embodiment in which the pin 25 is provided for a hermetically sealed battery, the pin may be made of a titanium alloy (e.g., Grade 5, Grade 9, or SP700). According to another exemplary embodiment, the pin could also include aluminum.

According to an exemplary embodiment in which the pin 25 is provided for a non-hermetically sealed battery, it may include a crimped or "rivet feedthrough" with a polymer grommet. The rivet portion would be the same material as listed above for hermetically sealed batteries. The polymer may be a polyolefin (e.g., a low-creep material such as polypropylene or HDPE) or may be ETFE.

According to an exemplary embodiment, the negative active material may be selected from graphite, $Li_4Ti_5O_{12}$, lithium alloying elements such as aluminum, tin, and silicon, and combinations thereof, and the positive active material may be selected from $LiCoO_2$; $LiM_x Ni_{1-x}O_2$ (where M is a metal such as Ti or Al); $LiMn_2O_4$; $LiCo_xMn_yNi_zO_2$ (where $x+y+z=1$), and combinations thereof.

Various components of the implantable medical device 100 may also be made from materials that are less likely to produce significant MRI image distortion. For example, screws and set screw blocks conventionally used in assembling the device 100 are formed of stainless steel, which has a significant ferrous content. According to an exemplary embodiment, the device 100 utilizes connectors that are formed from a material (e.g., titanium or a titanium alloy, a polymeric material such as polysulfone or polyether ether ketone, etc.) that is both biocompatible and has a reduced tendency to distort MRI images.

Implantable medical devices such as that shown in FIG. 4 may also utilize one or more electrical contacts (not shown) within the device. Presently, such contacts are provided in the form of platinum spring contacts (referred to as Bal-seals) inside of housings made from an alloy including chromium, cobalt, molybdenum, and nickel. According to an exemplary embodiment, the device 100 utilizes a low permeability stainless steel (e.g., having a permeability of between approximately 1.008 and 1.02) in place of the alloy formerly used to produce the housing. According to another exemplary embodiment, the housing may be made of platinum or a platinum alloy. According to yet another exemplary embodiment, the housing may be made of a creep resistant polymer (e.g., polysulfone or thermoplastic polyether ether ketone (referred to as PEEK)). One advantageous feature of utilizing a polymer is that doing so would not only reduce the image distortion due to the use of ferrous materials, but it would also eliminate the image distortion caused by eddy currents. According to still yet another exemplary embodiment, the housing may be made of a platinum-clad titanium material.

The wiring board or hybrid 130 includes various features such as electronic chips and the like. Conventionally, such components may utilize ferrite materials (e.g., as cores for coils or inductors). According to an exemplary embodiment, the hybrid 130 is produced without the use of ferrite materials (e.g., telemetry and/or recharge antennas may utilize air core antennas).

Conventional bonding pads utilized with the hybrid 130 may be formed of nickel 200 or Kovar (an alloy of iron, nickel, and molybdenum). According to an exemplary embodiment, the bonding pads utilized with the hybrid may be formed of titanium, platinum, copper, or alloys thereof.

The coils 120 utilized with the device 100 have conventionally been formed of copper, and have included ferrite cores. Because copper has a permeability close to that of water, and acts as an excellent conductor, it may be desirable to continue to use copper for the coils 120. According to an exemplary embodiment, copper coils with air cores are used in place of the copper coils with ferrite cores used in conventional designs. According to other exemplary embodiments, a member or element such as a ring of shimming material (e.g., platinum, aluminum) may be provided adjacent the coil or at a location proximate the coil.

The device enclosure 140 has conventionally been made of grade 1 titanium, which has a permeability that is relatively close to that of water. However, because the device enclosure 140 has a relatively large surface area, relatively significant eddy currents can be created on it during an MRI scan, which may result in image distortion. In order to reduce the eddy currents formed during an MRI scan, the device enclosure may be formed of a titanium having a higher resistivity. For example, according to an exemplary embodiment, the device enclosure may utilize a grade 9 titanium (or another grade or alloy of titanium having a higher resistivity).

According to other exemplary embodiments, different materials may be used to form the device enclosure 140. For example, according to an exemplary embodiment, the enclosure is constructed out of a polymer and then covered using a diamond-like coating for hermeticity. It is expected that such a construction would significantly reduce the eddy currents created on the enclosure during a scan and the resulting image distortion. According to another exemplary embodiment, the device enclosure 140 may be constructed using a creep resistant polymer such as thermoplastic polyether ether ketone or polysulfone, which would completely eliminate the eddy currents created on the enclosure during a scan.

According to other exemplary embodiments, the device enclosure 140 may be formed such that is includes a variety of thicknesses to create reflections that reduce the loop area of the eddy currents during a scan. For example, the enclosure 140 may be made with areas (e.g., zones, regions, etc.) that are thinner than surrounding areas to further increase the electrical resistivity to minimize eddy currents. According to one exemplary embodiment, the enclosure 140 may be produced in a metal injection molding process (e.g., in which a titanium housing is injection molded) such that a plurality of areas or regions of the housing are formed as having different thicknesses. According to another exemplary embodiment, the housing may have a substantially uniform thickness and have components coupled (e.g., welded) thereto to increase the thickness of particular regions of the housing (e.g., a titanium housing may have titanium, platinum, or aluminum strips of material welded thereto).

Extensions, tethers, or other accessories may be constructed using materials that do not cause significant image distortion. For example, according to an exemplary embodiment, extensions or tethers may be constructed using platinum irridium filers and contacts.

According to an exemplary embodiment, all or a portion of an implantable medical device such as an INS may be shimmed using materials having known magnetic permeabilities in order to decrease image distortion when an organism in which the device 100 is implanted undergoes an MRI scan. For example, if a device has a relative magnetic permeability that makes it paramagnetic overall, it may be advantageous to provide a diamagnetic shimming material in order to "balance" the paramagnetic character of the device, thus bringing the overall magnetic permeability of the device closer to that of water. Shimming may be accomplished in any number of ways, including coating or plating (e.g., cladding) the device or portions thereof with a shimming material (e.g., a titanium housing may be shimmed with platinum or palladium). Another manner in which shimming may be accomplished is by providing components within the device that have desired shimming properties. These and other methods of shimming a medical device will be described hereafter with reference to the accompanying drawings. Materials used to shim the device may be selected based on a variety of considerations including their magnetic permeability characteristics and biocompatibility, and may include, for example, titanium, palladium, platinum, silver, copper, manganese, aluminum, and alloys and combinations thereof.

While the goal of shimming the implantable medical device with a shimming material is to produce a device that has a magnetic permeability as close to water as possible (and thus, as close as possible to that of the organism into which it will be implanted), in some circumstances it may be adequate to simply add some shimming material such that there is less MRI image distortion than if no shimming material were added. The degree of acceptable MRI image distortion that is acceptable or suitable in a given circumstance may vary depending on the location of the device implantation and other factors, and the amount of shimming material added to the device should be selected such that it is adequate to provide a suitably small amount of image distortion under the circumstances.

According to an exemplary embodiment, a method of determining the appropriate amount of shimming material to be added to an implantable medical device includes creating a prototype of the device and creating an electromagnetic model of the device prototype. The prototype may then be analyzed to determine the aggregate relative magnetic permeability of the device prototype (e.g., by viewing the field perturbation in a magnetic field). Based on the aggregate relative magnetic permeability of the device prototype, it may be determined whether the shimming material should be paramagnetic or diamagnetic. The appropriate shimming material may then be selected and added to the device prototype. After the shimming material is added to the device prototype, the device may be re-modeled to determine its new aggregate relative magnetic permeability. Shimming material may again be added and the device re-modeled in an iterative manner until the desired level of aggregate magnetic permeability is reached.

Figure 7:
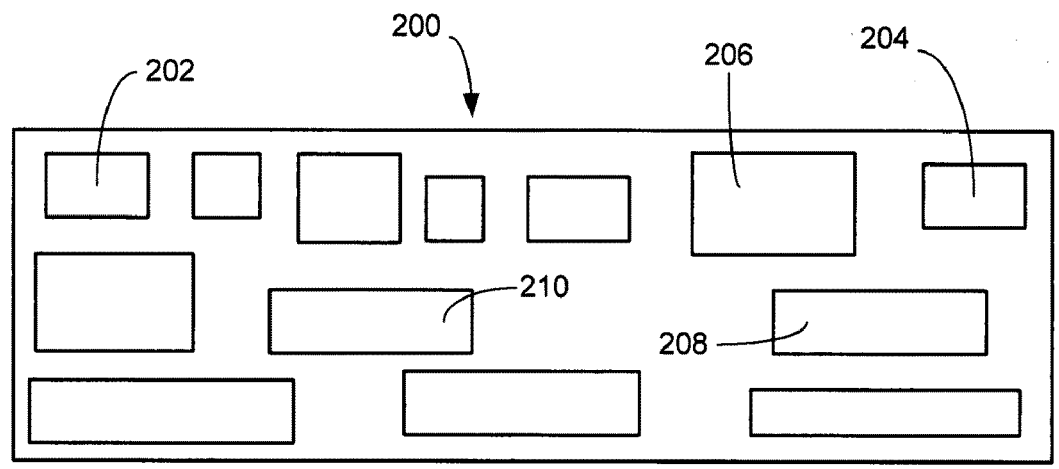
FIG. 7 is a schematic plan view of a hybrid or circuit board in which components that may cause MRI image distortion are not provided adjacent one another.

To determine the proper placement of the shimming material, it is desirable to first understand which components of the device are most likely responsible for the image distortion (i.e., the "problem components"). To enhance the ability of the shimming material to perform its desired function, it may be beneficial to design the device such that the problem components are not grouped together, but rather are spread apart. FIG. 7 illustrates a circuit board or hybrid 200 that includes two problem components 202 and 204. As illustrated, the problem components 202 and 204 are not provided proximate or adjacent one another, but rather are spread out such that they are on opposite ends of the hybrid 200 to reduce the amount of localized image distortion caused by the components. The particular placement and location of the problem components may vary according to various exemplary embodiments.

According to another exemplary embodiment, problem components may be provided proximate or adjacent to other components that have opposite magnetic permeabilities (e.g., a paramagnetic component may be provided next to one or more diamagnetic components) in order to provide some degree of localized cancellation of the undesirable effect caused by the components (e.g., to effectively "shim" the problem components). For example, as shown in FIG. 7, if component 204 is diamagnetic, components 206 and 208 may be paramagnetic.

Figure 8:
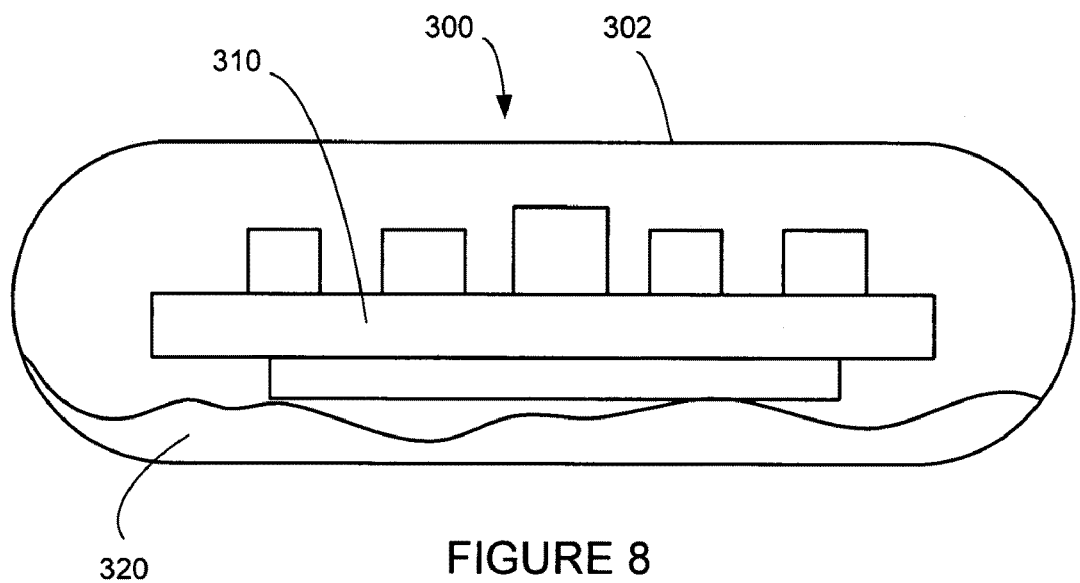
FIG. 8 is a schematic cross-sectional view of an implantable medical device according to an exemplary embodiment in which a potting material or adhesive includes a shimming material provided therein.

According to other exemplary embodiments, shimming materials may be incorporated within other materials used within an implantable medical device. For example, as shown in FIG. 8, an implantable medical device 300 includes a housing or casing 302 in which a hybrid or circuit board 310 is provided. A potting or filler material 320 may be provided within the device 300, with a shimming material provided or loaded in the potting material 320. According to an exemplary embodiment, the potting material is made of epoxy or silicon rubber and has a suitable shimming material provided therein (e.g., if the device is paramagnetic overall, a diamagnetic material such as silver may be incorporated in the potting material).

Similar to the embodiment shown in FIG. 8, an epoxy or other adhesive used to secure various components within the device 300 may include a shimming material provided or loaded therein. One advantageous feature of providing shimming material in a potting material or in an adhesive provided within the housing 302 of the device 300 is that there is little or no impact on the size of the device, since the shimming materials would be provided in spaces that are either unoccupied or in materials that are already used in the device.

Other components of the device may also be loaded with a shimming material. For example, as shown in FIG. 4, an insulator cup 170 is provided in the device 100 for housing certain components of the device 100. According to an exemplary embodiment, the insulator cup 170 may be loaded with a shimming material in order to improve the permeability of the device 100.

Figure 9:
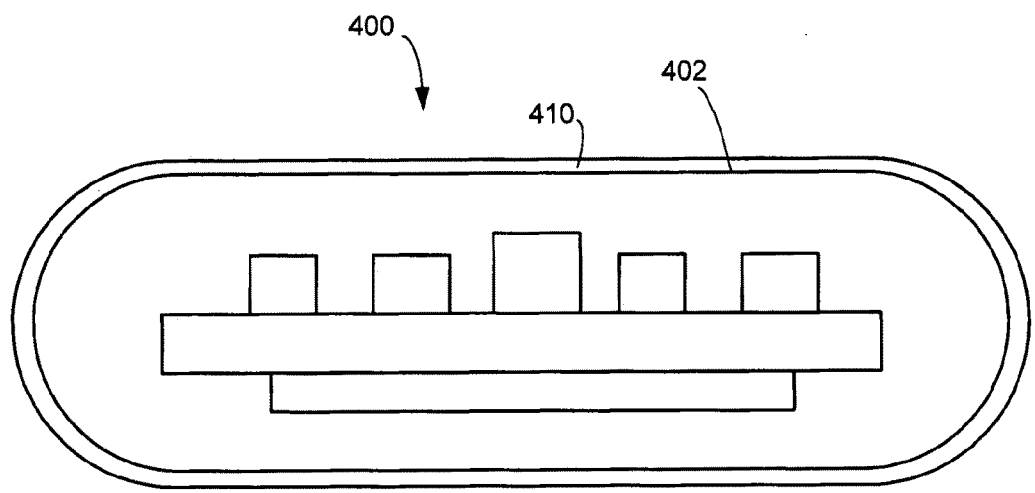
FIG. 9 is a schematic cross-sectional view of an implantable medical device according to an exemplary embodiment illustrating a shimming material provided as a plating provided on the inner surface of the device housing.
Figure 10:
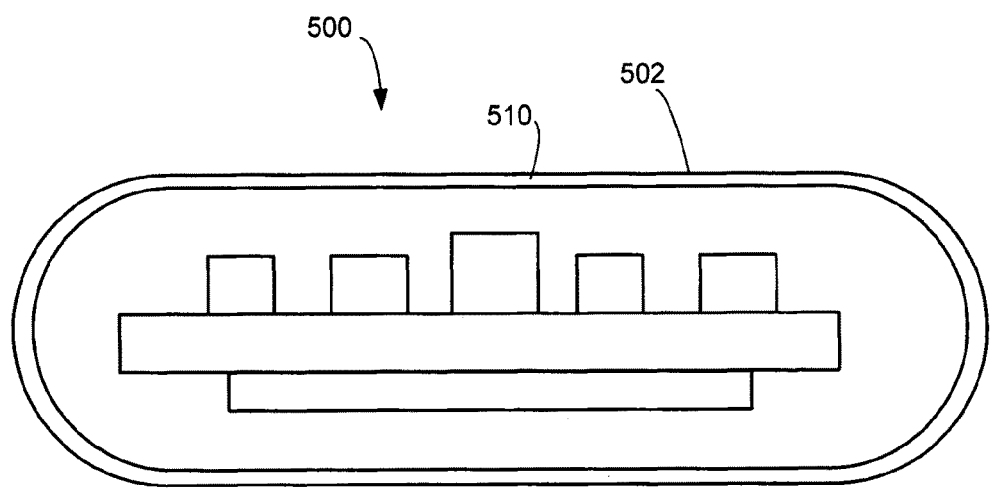
FIG. 10 is a schematic cross-sectional view of an implantable medical device according to an exemplary embodiment illustrating a shimming material provided as a plating provided on the outer surface of the device housing.

According to other exemplary embodiments, all or a portion of the device enclosure may be coated, plated, or clad with a shimming material. FIGS. 9 and 10 illustrate a shimming material coated (e.g., plated, clad, etc.) on a housing of an implantable medical device according to two exemplary embodiments. FIG. 9 illustrates a device 400 having a housing or casing 402 with a shimming material 410 provided on an outer or exterior surface of the housing 402. FIG. 10 illustrates a device 500 having a housing or casing 502 with a plating or coating 510 provided on an inner or interior surface of the housing 502. According to an exemplary embodiment, the housings shown in FIGS. 9 and 10 are made from a paramagnetic material, and the shimming material is made from a diamagnetic material. According to other exemplary embodiments, the housings may be made of paramagnetic materials and the shimming material may be a diamagnetic material.

It should be noted that where the shimming material is provided on an exterior surface of the device housing, it is advisable to ensure that the material selected for the plating or coating material be biocompatible with the organism into which the device is to be implanted. The thickness of the shimming material may vary according to various exemplary embodiments. According to an exemplary embodiment, the shimming material has a thickness of between approximately 0.005 inches (0.125 mm) and 0.040 inches (1 mm).

While FIGS. 9 and 10 illustrate a shimming material provided on either the exterior or interior surface of the housing, it should be noted that shimming material may be provided on both the exterior and interior surfaces (and further, that only a portion of the exterior and/or interior surfaces may have shimming materials provided thereon). The shimming materials provided on the exterior surface and the interior surface may have identical or different compositions. Further, more than one type of shimming material may be provided on the exterior and/or interior surfaces of the housing (e.g., silver may be provided on a portion of the exterior surface and titanium on another portion, etc.).

According to a particular exemplary embodiment, the interior and/or exterior of a housing for an implantable medical device is at least partially coated (e.g., clad, plated, etc.) with titanium or a titanium alloy to a thickness sufficient to reduce or minimize image distortion caused by the device enclosure. According to another particular exemplary embodiment, the interior and/or exterior of a housing for an implantable medical device is at least partially coated (e.g., clad, plated, etc.) with silver or a silver alloy to a thickness sufficient to reduce or minimize image distortion caused by the device enclosure (e.g., up to approximately 0.005 inches).

Figure 11:
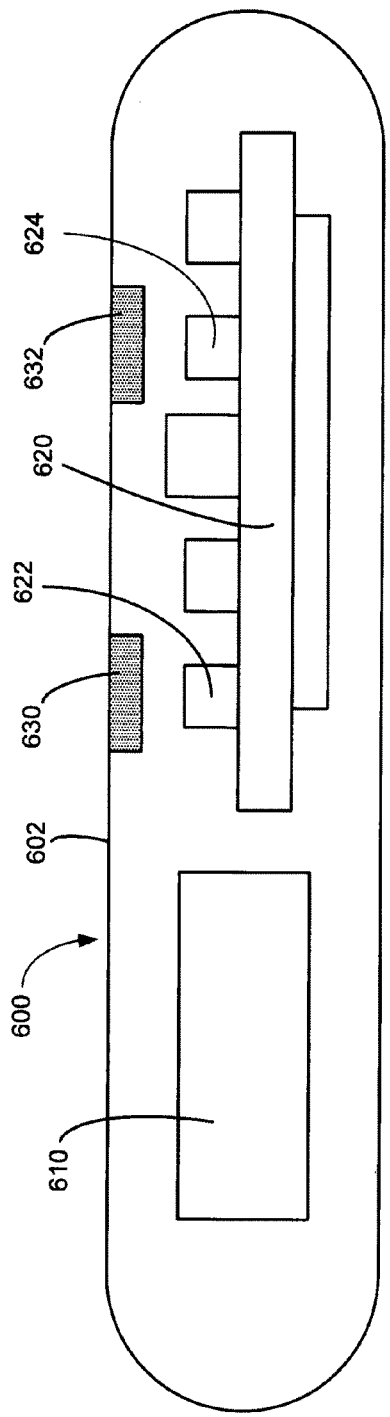
FIG. 11 is a schematic cross-sectional view of an implantable medical device according to an exemplary embodiment illustrating a shimming material provided on a portion of the device housing or casing.

While FIGS. 9 and 10 illustrate embodiments in which the entire interior and/or exterior surfaces of the device housings are coated or plated with a shimming material, it should be noted that according to other exemplary embodiments, the shimming or plating material may be provided on only a portion of the housing or casing. As shown in FIG. 11, an implantable medical device 600 includes a battery 610 and a hybrid or circuit board 620 provided within a housing or casing 602. The hybrid 620 includes two components 622 and 624 that are most responsible for producing image distortion in an MRI image (i.e., they are so-called "problem components"). Shimming materials are providing on housing 602 only in locations proximate or adjacent to the problem components 622, 624 (shown as regions or areas of shimming materials 630 and 632). In this manner, the shimming material is placed in the location where it may be most efficacious in reducing the amount of MRI image distortion caused by the problem components. One advantage of such a configuration is that the amount of shimming material required to provide adequate shimming of the device may be more closely tailored to the amount actually needed, which may result in less shimming material being used than if the entire interior and/or exterior surface of the housing were coated with the shimming material. The provision of separate regions of coating or plating on the device housing may accomplished using masking techniques or any other suitable technique.

Figure 12:
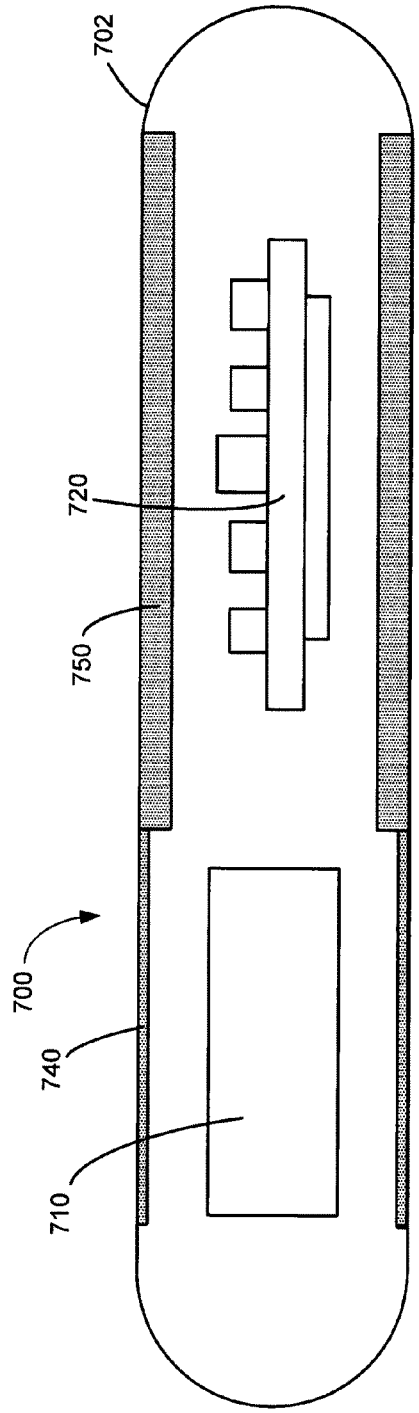
FIG. 12 is a schematic cross-sectional view of an implantable medical device according to an exemplary embodiment illustrating a shimming materials having differing thicknesses provided on the device housing.

The thickness of the shimming material may vary according to various considerations, including the particular amount of shimming needed at a particular location within the housing. FIG. 12 illustrates an implantable medical device having a housing 702 with a battery 710 and a hybrid or circuit board 720 provided therein. In the embodiment shown, the battery 710 has been determined to be less responsible for MRI image distortion than the hybrid 720. Accordingly, a greater amount of shimming material is provided proximate or adjacent the hybrid 720 as compared to that provided adjacent the battery 710. This is illustrated by a first plated or coated shimming material 740 having a first thickness provided adjacent the battery 710 and a second plated or coated shimming material 750 provided adjacent the hybrid 720. According to an exemplary embodiment, the two shimming materials 740 and 750 have the same composition. According to other exemplary embodiments, the shimming materials 740 and 750 have different compositions (e.g., shimming material 740 may comprise platinum, while shimming material 750 may comprise aluminum). The composition of the shimming materials and the coating/plating thicknesses selected will vary according to various exemplary embodiments in accordance with the necessary amount of shimming in particular regions within the housing.

In certain cases, providing a shimming material in the form of a coating or plating on the device housing may adversely affect charging or telemetry of the device. In such cases, it may be desirable to provide the coatings in a manner that will not affect such functions. For example, FIGS. 13-14 illustrate schematic views of an implantable medical device 800 according to an exemplary embodiment. Device 800 includes a housing or casing 802 having a battery 810 and a hybrid or circuit board 820 provided therein. A recharging or telemetry coil 812 is provided proximate the battery 810. To reduce or eliminate the adverse effect that may be caused by coating of the housing 802, coating is not provided in the areas of the housing proximate the recharging or telemetry coil 812. As shown in FIG. 14, coatings 830 and 832 are provided adjacent the battery and coatings 834 and 836 are provided adjacent the hybrid 820. Spaces are provided between coatings 830 and 834 and between coatings 832 and 836 in the regions 840, 842, and no coating is provided in regions 844 and 846. In this manner, no coating is provided in regions 840, 842, 844, and 846 proximate the recharging/telemetry coil. The selective coating of the housing may be accomplished by masking or other suitable methods.

The plating or coating of the device housings as shown in FIGS. 9-14 may be accomplished by any suitable method (e.g., PVD, CVD, sintering, etc.). According to an exemplary embodiment, a paramagnetic material is coated on the device housings by physical vapor deposition. It should also be noted that while FIGS. 11-14 illustrate plating on the inner surface of the device housings, similar results may be obtained by coating or plating the exterior surface of such devices (e.g., the coating shown within the housings in FIGS. 11-14 may instead be provided on an exterior surface of the housing).

It should be noted that features shown in FIGS. 8-14 may be combined as may be desired. For example, the embodiment shown in FIG. 14 may be modified to include coatings having different thicknesses (as shown, e.g., in FIG. 12) and/or to have coatings provided adjacent problem areas (as shown, e.g., in FIG. 11 with respect to problem areas-adjacent the hybrid). A potting material loaded with a shimming material may also be used. Various combinations of such features are possible, and all such combinations are intended to fall within the scope of the present disclosure.

Figure 15:
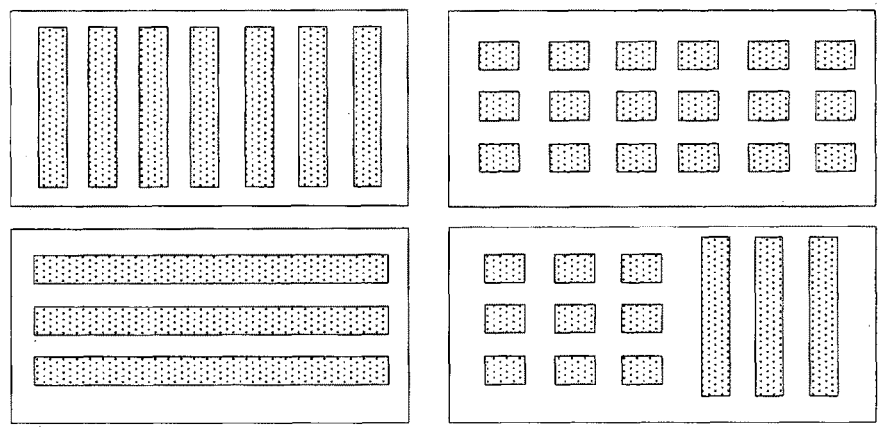
FIG. 15 is a drawing illustrating several possible coating or plating patterns that may be used to provide a shimming material on an implantable medical device.

Any of a variety of coating methods may be used to provide shimming material on all or a portion of a component such as the housing. For example, all or a portion of the housing may be completely coated with a shimming material. According to other exemplary embodiments, the coating may be applied as having any of a variety of patterns using masking or other techniques that are now known or may be hereafter developed. FIG. 15 illustrates four coating patterns (formed, e.g., using masking techniques or other suitable techniques) that may be applied to all or a portion of a component according to various exemplary embodiments, although it should be understood that numerous other patterns may be possible. Additionally more than one different type of pattern may be applied to the same component.

Figure 16:
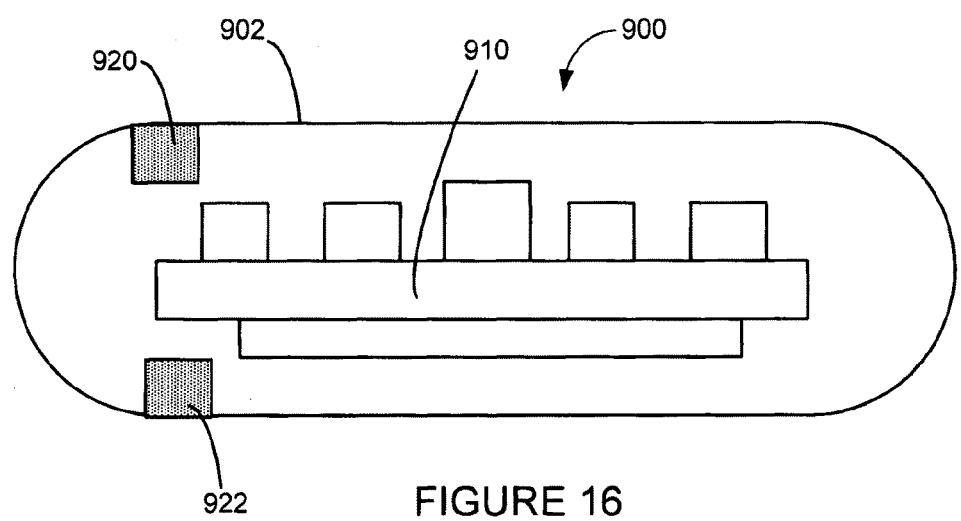
FIG. 16 is a schematic cross-sectional view of an implantable medical device according to an exemplary embodiment having shimming components coupled to the device housing.

As an alternative to (or in addition to) plating or coating the housing with a shimming material, pieces (e.g., members, elements, etc.) of shimming material may be coupled to the housing by welding, soldering, adhesive, or by any other suitable method. FIG. 16 illustrates a schematic cross-sectional view of an implantable medical device 900 having a housing 902 having a hybrid or circuit board 910 provided therein. Two pieces of shimming material 920 and 922 are coupled to an interior surface of the housing 902 in areas unoccupied by components of the device 900. Any number of shimming components may be coupled to the housing having any of a variety of sizes, shapes, and/or configurations according to various exemplary embodiments.

Figure 17:
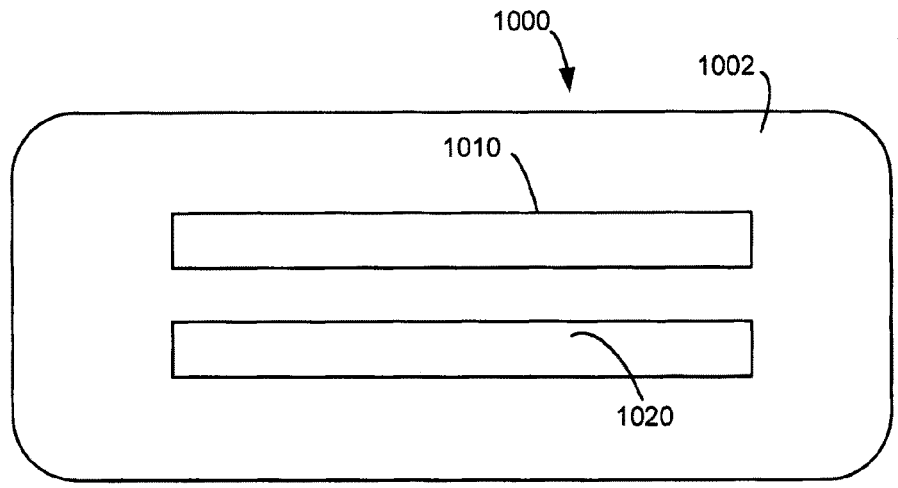
FIG. 17 is a schematic plan view of an implantable medical device having shimming components provided on the exterior surface of the device according to an exemplary embodiment.

FIG. 17 illustrates a schematic plan view of an implantable medical device 1000 according to another exemplary embodiment. The device 1000 includes a hermetically sealed housing or casing 1002 that has rails 1010 and 1020 welded to the exterior surface thereof. The rails 1010 and 1020 are made of titanium according to an exemplary embodiment and have a shimming material loaded into the rails. According to an exemplary embodiment, the rails have a thickness of between approximately 1 mm and 4 mm, although the size, shape, and/or configuration of the rails may vary according to other exemplary embodiments. According to other exemplary embodiments, the rails may be coupled to an interior surface of the housing. According to an exemplary embodiment, the shimming material is encapsulated in a biocompatible material to avoid direct tissue contact and corrosion.

Figure 18:
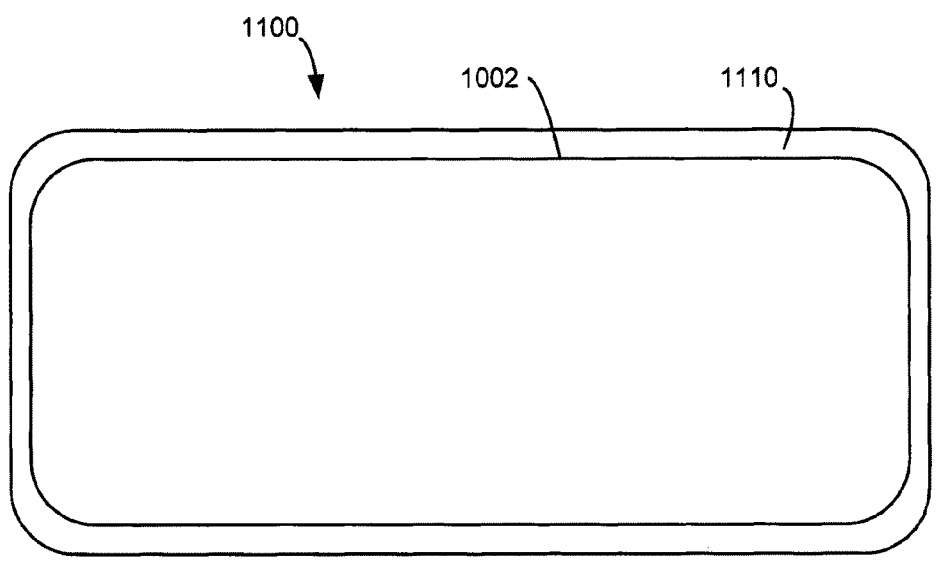
FIG. 18 is a schematic cross-sectional view of an implantable medical device according to another exemplary embodiment.

Other shimming components can also be provided exterior to the housing or casing of an implantable medical device. For example, FIG. 18 illustrates an implantable medical device 1100 according to another exemplary embodiment having a shimming component 1110 coupled to an exterior surface of its housing or casing 1102. According to an exemplary embodiment, the shimming component 1110 is a polymeric material loaded with a shimming material that is molded directly to the housing 1102 (e.g., where a housing of a device is made of titanium or a titanium alloy, the polymeric material may be an epoxy loaded with a diamagnetic material such as silver or a silver alloy, although the particular constituents may differ according to other exemplary embodiments; additionally, the polymeric material may be provided on the interior surface of the housing). According to another exemplary embodiment, the component 1110 is a boot that surrounds the housing 1102 (e.g., the boot may be a silicon rubber (or similar material) boot that has a shimming material incorporated therein). According to yet another exemplary embodiment, the component 1110 is a paralyne coating that has incorporated therein a shimming material (again, it should be noted that the paralyne coating may be provided on the interior surface of the housing). It should be noted that while FIG. 18 illustrates component 1110 as completely surrounding the housing 1102, according to other exemplary embodiments, the component 1110 may only partially surround the housing 1102 (e.g., the component may be provided at only select locations on the exterior surface of the housing 1102).

As an alternative to or in addition to shimming all or a portion of the medical device housing or casing, it may also be possible to provide shimming materials on structures or elements included within the medical device housing. For example, because the battery 10 is provided within the device enclosure 140, and is therefore not in direct contact with the human body in which the device 100 is implanted, it may be desirable to plate or coat the exterior surface of the battery 10 with a shimming material (e.g., a diamagnetic material). According to an exemplary embodiment, at least a portion of an interior or exterior surface of a titanium or titanium alloy battery housing 20 is coated (e.g., clad, plated, etc.) with silver or a silver alloy to a thickness sufficient to reduce image distortion caused by the housing 20 (e.g., between approximately 0.0001 and 0.01 inches). According to another exemplary embodiment in which a battery housing 20 is made of copper or a copper alloy, the housing 20 may be coated (e.g., clad, plated, etc.) with titanium or titanium alloy to a thickness sufficient to reduce image distortion caused by the housing 20 (e.g., between approximately 0.0001 and 0.01 inches). It should be noted that all or a portion of the interior and/or exterior surface of the battery housing may be plated or coated with a shimming material, and that the coating and plating methods described herein with respect to FIGS. 8-18 may be utilized as may be appropriate in a particular battery configuration (e.g., two or more portions of the housing may be plated with different amounts of shimming material, as shown for example in FIG. 12 in the context of an implantable medical device).

According to another exemplary embodiment, a non-functional shimming component (e.g., a shimming member or element) may be added to a hybrid or circuit board (e.g., hybrid 200) to shim the hybrid. For example, as shown in FIG. 7, a shimming component 210 (e.g., member, element, etc.) is added directly to the hybrid in order to shim the hybrid. The component 210 serves no electronic purpose for the hybrid, and in effect is a "dummy" component (e.g., a block of shimming material) provided for the purpose of shimming the hybrid 200. The component 210 may be provided in any suitable location on the hybrid (e.g., adjacent to another component that would benefit from being shimmed, in a blank area on the hybrid, etc.). The size, shape, and/or configuration of the component 210 may vary according to other exemplary embodiments. It should also be noted that more than one such component may be provided on the hybrid. One advantageous feature of providing shimming components directly on the hybrid is that the size of the device need not be increased to accommodate the shimming component (since the hybrid has a fixed size, and the shimming components fit in otherwise unused space on one or both sides of the hybrid).

Figure 19:
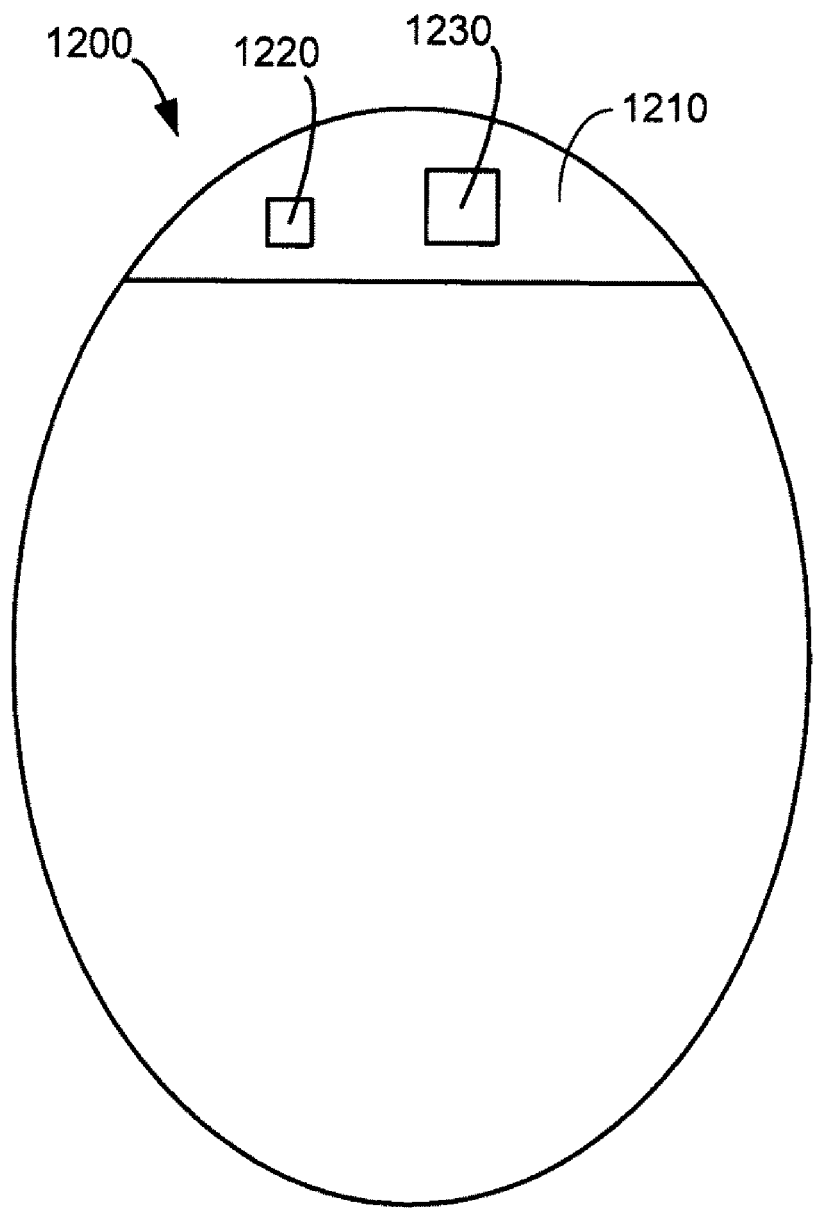
FIG. 19 is a schematic plan view of an implantable medical device according to an exemplary embodiment having shimming components provided in a header block.

According to another exemplary embodiment, an implantable medical device includes a header block that includes a number of metallic components for use by the device. FIG. 19 is a schematic plan view of a device 1200 that includes a header block 1210. Shimming components 1220 and 1230 may be provided within the header block to shim other metallic components provided in the header block and/or to shim the device as a whole. One advantageous feature of providing shimming components within the header block is that the shimming components are provided in relatively close proximity to the metallic components in the header block.

The type of MRI scan can also be designed to reduce distortion. Different types of scans can have different effects on the image distortion. For example, a gradient echo pulse sequence is disadvantageous for mitigating image distortion and a spin echo sequence is superior. Further, a technique called shimming can also be used to address image distortion. Image distortion is better on lower static magnetic field strength machines and is worse on higher static magnetic field strength machines. Ways to minimize the image distortion through the scan type, image processing, and shimming will be described in detail below.

According to an exemplary embodiment, the MRI machine and associated image processing system are used to address the image distortion resulting from an implant, such as a cranial implant. The adjustments may further reduce the distortion resulting from such a device after applying one or more of the other features of the invention discussed above. In particular, the pulse sequence selection, certain image processing techniques, and shimming may all be used to address or counteract distortions resulting from the implant.

Image artifacts from metallic implants are highly dependent on the choice of pulse sequence. The particular MRI pulse sequence may be selected to reduce image distortion. There are several commonly used pulse sequences in diagnostic MRI imaging. These include gradient echo, spin echo, and fast spin echo pulse sequences, among others. Spin-echo pulse sequences are inherently less susceptible to magnetic field distortion artifacts relative to gradient echo sequences.

Therefore, a spin echo sequence may be selected to reduce image distortion associated with the implant.

Image processing techniques may also be utilized to address image distortion associated with an implanted cranial device. For example, image processing software may be used to correct for known distortions. In addition to a general application of image processing techniques to correct for distortion, in a preferred embodiment, techniques are utilized that are applicable to a specific implanted device. Such techniques may include using known factors, such as material composition, size, and implanted location, in a processing algorithm to compensate for distortion associated with a specific implanted device. In practice, the necessary image processing algorithm may be determined experimentally by acquiring images of a specific device implanted in a phantom to provide the necessary correction data.

Yet another imaging approach that may be utilized to address cranial image distortion is the use of a wider bandwidth for the imaging gradients.

Shimming techniques may also be utilized to address magnetic field inhomogeneity due to an implant, such as device 100. Ideally, the magnetic field gradients associated with the presence of an implanted device may be addressed through the use of shim coils to correct the field inhomogeneity. Shim coils are designed and placed on an MRI or an NMR machine to actively compensate for magnetic field inhomogeneities, doing so by providing "canceling" magnetic fields when current is run through the shim coils. Adjusting the currents in such shim coils to cancel the unwanted gradients is known as "active shimming." Various active shimming approaches are known and used, especially in NMR spectroscopy. However, there is a need for the ability to correct for magnetic field inhomogeneities in MRI, and certain NMR shimming principles and devices may be applied in accordance with the present invention.

Certain conventional MRI machines utilize shim coils to correct for the magnetic field inhomogeneity due to placement of the patient in the field. The shim coils are intended to address first order gradients due to the patient, i.e., to correct for the linear variation in magnetic field strength with position due to the presence of the patient in the field. Such shim coils may be useful to adjust the field inhomogeneities due to an implant using approaches in accordance with certain embodiments of the present invention. However, implants, especially those including ferromagnetic materials, may result in higher order gradients, e.g., second order gradients having quadratic variations in field strength. The active shim coils presently in use on MRI machines to correct first order gradients may not suitably address the second order gradients associated with an implant. Accordingly, in an embodiment of the present invention, additional shim coils are installed and utilized to correct for the presence of the implant. Likewise, additional shim coils may be utilized to correct higher order gradients, depending on the desired level of correction.

Active shimming may be performed manually by changing the current supplied to various shim coils to achieve the best gradient correction. However, computers have been used to automate such shimming with varying degrees of success because the process of shimming tends to be complex and tedious, especially due to the interactions between multiple shim coils when correcting second and higher order gradients.

According to an exemplary embodiment, a custom shim for the implant is utilized. The custom shim may be created because the device properties are known and therefore may be specifically addressed by an active shimming technique. In a preferred embodiment, custom software may be utilized to automate the active shimming, and may be customized for a specific cranial device, and/or a specific MRI machine.

According to an exemplary embodiment, the distortion associated with the implant is mitigated as follows. A patient having an implant is positioned in an MRI machine for image acquisition. Prior to imaging, shim coils are used to adjust the magnetic field to address unwanted gradients in the field caused by the implant (and patient). The adjustment may include the use of shim coils to address first order gradients or may involve adjusting the current in multiple shim coils to address first order, second order, and even higher order gradients. Once the field inhomogeneities have been addressed via active shimming (either manually, or automatically, utilizing custom shimming software or other automating techniques), the image may be acquired, preferably by utilizing a spin echo pulse sequence. Once the data has been acquired, the image may be reconstructed using conventional reconstruction techniques that are modified to adjust for known distortions associated with the implant, such as the use of a custom image processing routine to adjust for the specific implanted device.

While the implantable medical device is described herein in the context of an implantable neurological stimulation device, it should be understood that other types of implantable medical devices may also benefit from the use of the features described herein, including, by way of example, implantable defibrillators, pacemakers, cardioverters, cardiac contractility modulators, drug administering devices, diagnostic recorders, cochlear implants, and the like.

It is important to note that the construction and arrangement of the implantable medical devices as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present invention. The order or sequence of any process or method steps may be varied or re-sequenced according to alternative embodiments. Other substitutions, modifications, changes and omissions may be made in the design, operating conditions and arrangement of the various exemplary embodiments without departing from the scope of the present inventions.

What is claimed is:

1. A lithium battery comprising:
a housing;
a first electrode provided within the housing;
a first tab coupled to the first electrode;
a second electrode provided within the housing;
a second tab coupled to the second electrode;
a pin coupled to the second tab and extending to a location outside the housing; and
a bracket provided within the housing to couple one of the first tab and the second tab to the housing, the bracket comprising a material comprising vanadium.

2. The lithium battery of claim 1, wherein the pin is formed from a material comprising vanadium.

3. The lithium battery of claim 1, wherein the second tab is formed from a material comprising vanadium.

4. The lithium battery of claim 1, wherein the first tab is formed from a material comprising vanadium.

5. The lithium battery of claim 1, wherein the second tab and the pin are formed from a material comprising vanadium.

6. The lithium battery of claim 1, wherein the material comprising vanadium is a vanadium alloy.

7. The lithium battery of claim 1, wherein the second tab is formed from a material comprising vanadium and the second electrode comprises copper.

8. The lithium battery of claim 1, wherein the housing comprises a material selected from the group consisting of aluminum, titanium, copper, and alloys and combinations thereof.

9. The lithium battery of claim 1, wherein the housing comprises an aluminum foil and polymer composite material.

10. The lithium battery of claim 1, wherein the battery is configured for use in an implantable medical device.

11. The lithium battery of claim 1, wherein the implantable medical device is an implantable neurological stimulation device.

12. A lithium battery comprising:
   a housing;
   a first current collector electrically coupled to a positive electrode;
   a second current collector electrically coupled to a negative electrode;
   a terminal coupled to one of the first current collector and the second current collector; and
   a member within the housing coupling the second current collector to the housing, wherein the member comprises a material selected from the group consisting of vanadium and vanadium alloys.

13. The lithium battery of claim 12, wherein the terminal comprises vanadium and is coupled to the second current collector.

14. The lithium battery of claim 12, wherein the second current collector comprises vanadium.

15. The lithium battery of claim 12, wherein the terminal and the second current collector comprise vanadium.

16. The lithium battery of claim 12, wherein the first current collector comprises vanadium and the potential of the positive electrode is less than approximately 3.6 volts.

17. The lithium battery of claim 12, wherein the terminal comprises titanium and the second current collector comprises vanadium.

18. The lithium battery of claim 12, further comprising a housing comprising a material selected from the group consisting of aluminum, titanium, copper, and alloys and combinations thereof.

19. The lithium battery of claim 18, wherein the housing comprises an aluminum foil and polymer composite material.

20. The lithium battery of claim 12, wherein the housing comprises titanium.

21. An implantable medical device comprising:
   a housing configured for implantation in a human body; and
   a lithium battery provided within the housing, the battery comprising a member formed of a vanadium material, the member coupling the housing to a tab that extends from an electrode.

22. The implantable medical device of claim 21, wherein the lithium battery comprises a terminal comprising a material selected from the group consisting of vanadium and vanadium alloys.

23. The implantable medical device of claim 21, wherein the tab comprises a material selected from the group consisting of vanadium and vanadium alloys.

24. The implantable medical device of claim 23, wherein the electrode is a negative electrode.

25. The implantable medical device of claim 23, wherein the lithium battery comprises a terminal comprising a material selected from the group consisting of vanadium and vanadium alloys.

26. The implantable medical device of claim 21, wherein the implantable medical device is selected from the group consisting of a defibrillator, a pacemaker, a cardioverter, a cardiac contractility modulator, a drug administering device, a diagnostic recorder, and a cochlear implant.

27. The implantable medical device of claim 21, wherein the implantable medical device is an implantable neurological stimulation device.

* * * * *